United States Patent [19]

Mase et al.

[11] Patent Number: 5,169,513
[45] Date of Patent: Dec. 8, 1992

[54] ELECTROCHEMICAL ELEMENT AND METHOD OF MAKING

[75] Inventors: Syunzo Mase, Aichi; Shigeo Soejima, Nagoya, both of Japan

[73] Assignee: NGK Insulators, Ltd., Japan

[21] Appl. No.: 689,667

[22] Filed: Apr. 23, 1991

Related U.S. Application Data

[63] Continuation of Ser. No. 449,044, Dec. 14, 1989, abandoned, which is a continuation of Ser. No. 740,429, Jun. 3, 1985, abandoned.

[30] Foreign Application Priority Data

Jun. 6, 1984 [JP] Japan .................................. 59-116228

[51] Int. Cl.$^5$ .......................................... G01N 27/407
[52] U.S. Cl. ......................................... 204/429; 204/412; 204/425; 204/426; 427/126.2; 427/126.3
[58] Field of Search ............... 204/424, 425, 426, 427, 204/428, 429, 412; 427/123, 126.2, 126.3

[56] References Cited

U.S. PATENT DOCUMENTS

| | | | |
|---|---|---|---|
| 4,219,359 | 8/1980 | Miwa et al. | 204/428 X |
| 4,297,192 | 10/1981 | Shinohara et al. | 204/428 |
| 4,298,573 | 11/1981 | Fujishiro | 204/426 X |
| 4,334,974 | 6/1982 | Muller et al. | |
| 4,354,912 | 10/1982 | Friese | |
| 4,476,008 | 10/1984 | Sano et al. | 204/425 |
| 4,487,680 | 12/1984 | Logothetis et al. | 204/425 |
| 4,505,790 | 3/1985 | Mase et al. | 204/429 X |
| 4,505,805 | 3/1985 | Mase et al. | 204/425 |
| 4,547,281 | 10/1985 | Wang et al. | 204/425 X |

FOREIGN PATENT DOCUMENTS

| | | |
|---|---|---|
| 0019731 | 12/1980 | European Pat. Off. |
| 0059933 | 9/1982 | European Pat. Off. |
| 0082372 | 6/1983 | European Pat. Off. |
| 0108179 | 5/1984 | European Pat. Off. |
| 2904069 | 8/1980 | Fed. Rep. of Germany |
| 3021745 | 12/1980 | Fed. Rep. of Germany |
| 2449887 | 7/1980 | France |
| 2087569 | 5/1982 | United Kingdom |

*Primary Examiner*—Nam X. Nguyen
*Attorney, Agent, or Firm*—Parkhurst, Wendel & Rossi

[57] ABSTRACT

An electrochemical element comprising a laminar structure which includes a porous first layer of fully-stabilized zirconia ceramic, a second layer of partially-stabilized zirconia ceramic, and at least one pair of electrodes. At least one of the at least one pair of electrodes is disposed between the first and second layers, and in contact with the first layer.

10 Claims, 3 Drawing Sheets

ELECTROCHEMICAL ELEMENT AND METHOD OF MAKING

This is a continuation of application Ser. No. 07/449,044 field Dec. 14, 1989, now abandoned, which is a continuation of Ser. No. 06/740,429 filed Jun. 3, 1985, now abandoned.

BACKGROUND OF THE INVENTION

1. Field of the Art

The present invention relates generally to an electrochemical element, and more particularly to an element including a multi-layer electrochemical cell which comprises a solid electrolyte body of zirconia ceramics.

2. Related Art Statement

There have been known various electrochemical devices, each of which includes an electrochemical element using solid electrolyte. These electrochemical devices are used, for example, as oxygen sensors to detect the oxygen concentration of an exhaust gas emitted from internal combustion engines of automotive vehicles. Typical examples of such oxygen sensors include an oxygen sensor which uses zirconia ceramics as an oxygen-ion conductive solid electrolyte material. Such an oxygen sensor operates to determine the oxygen concentration according to the principle of an oxygen concentration cell. Also known in the art are electrochemical devices or elements such as sensing and pumping elements for hydrogen, nitrogen, carbon dioxide, etc. In recent years, there has been an increasing trend that an electrochemical element used in such devices as indicated above incorporates an electrochemical cell of a laminar structure which comprises a layer of zirconia ceramics solid electrolyte, and an electrode or electrodes disposed in contact with a surface or surfaces of the zirconia ceramic layer.

In such an electrochemical element of a laminar or multi-layer type, a porous diffusion layer having a predetermined diffusion resistance is formed on a zirconia solid electrolyte layer, so as to cover an electrode disposed on the zirconia solid electrolyte layer, in order to control an atmosphere of a measurement gas to which the electrode is exposed for contact therewith. Such a diffusion layer is also assigned to function as a solid electrolyte layer through which a pumping current is caused to flow between a pair of electrodes, which are provided on opposite sides of the solid electrolyte layer. Further, the electrochemical element may include a porous protective layer for protecting the electrode on the zirconia solid electrolyte layer from direct exposure to the measurement gas.

Also, it is known that the solid electrolyte layer of an electrochemical cell is formed of partially-stabilized zirconia ceramic having a tetragonal crystal phase or a monoclinic crystal phase, to improve thermal-shock resistance characteristics of the solid electrolyte layer. In the case where the solid electrolyte layer of partially-stablized zirconia ceramic is used in combination with a porous diffusion or protective layer or a porous diffusion-solid electrolyte layer (diffusion layer also serving as a solid electrolyte layer) as previously indicated, such a porous layer suffers severe changes in mechanical strength and electrical properties during its use, if the porous layer is made of partially-stabilized zirconia ceramic of the same composition as that used for the solid electrolyte layer. The changes are severe, particularly when a porous diffusion layer is formed of a partially-stabilized zirconia ceramic material. In this case, micro-cracks appearing on the surface of the partially-stabilized porous zirconia ceramic will develop into a serious problem, viz., internal destruction or collapse of the porous structure of the diffusion layer, which results in changing the diffusion resistance and thereby degrading the accuracy of measurement of the electrochemical element.

SUMMARY OF THE INVENTION

It is therefore an object of the present invention to provide an electrochemical element having improved characteristics of resistance to thermal shock or stress, which comprises a solid electrolyte layer of zirconia ceramic, and a porous layer formed on the zirconia ceramics solid electrolyte layer, wherein the porous layer is protected from physical changes and a change in electrical resistance.

According to the invention, there is provided an electrochemical element comprising a laminar structure which includes (a) a porous first layer of fully-stabilized zirconia ceramics, (b) a second layer of partially-stabilized zirconia ceramics, and (c) at least one pair of electrodes, at least one of the at least one pair of electrodes being disposed between the porous first layer and the second layer, and held in contact with the porous first layer.

In the electrochemical element of the present invention constructed as described above, a layer of zirconia solid electrolyte which serves as a substrate of the electrochemical element is made of partially-stabilized zirconia ceramic that is excellent in resistance to thermal shock, while a porous layer formed on the solid electrolyte layer is formed of a porous layer of fully-stabilized zirconia ceramic which is stable at elevated temperatures. The porous layer is effectively protected from physical changes and a change in electrical resistance. The use of partially-stabilized zirconia ceramics for the solid electrolyte substrate enables the electrochemical element as a whole to provide an increased mechanical strength, and an improved resistance to thermal shock or stress upon an abrupt change in temperature of the measurement gas or upon rapid heating of the element by a heater. Thus, cracks of the electrochemical element due to thermal stress are avoided.

According to an advantageous embodiment of the invention, the porous first layer of fully-stabilized zirconia ceramic consists substantially of a zirconia ceramics of cubic crystal phase, while the second layer of partially-stabilized zirconia ceramic consists substantially of zirconia ceramic having a tetragonal crystal phase, or of composite phase of tetragonal crystal and cubic crystal. In this case, a rate of thermal expansion of the second layer of partially-stabilized zirconia ceramic, i.e., solid electrolyte layer may exactly coincides with that of the porous first layer of fully-stabilized zirconia ceramics formed on the second layer. As a result, the electrochemical element is more effectively protected from flake-off or separation of the adjacent layers, cracking or other defects that may be caused by a difference in thermal expansion between the layers.

BRIEF DESCRIPTION OF THE DRAWING

The above and other objects, features and advantages of the present invention will become more apparent from reading the following detailed description of preferred embodiments of the invention, in connection with the accompanying drawings, in which.

DETAILED DESCRIPTION OF THE PREFERRED EMBODIMENTS

To further clarify the present invention, preferred embodiments of the invention will be described in detail by reference to the accompanying drawings.

Figure 1:
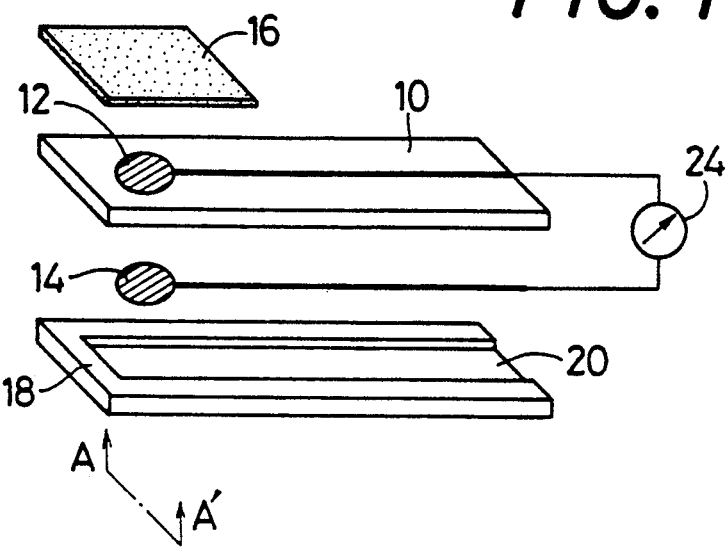
FIGS. 1, 3, 5, 7 and 9 are exploded perspective views of different embodiments of electrochemical elements of the invention in the form of oxygen concentration sensing elements.
Figure 2:
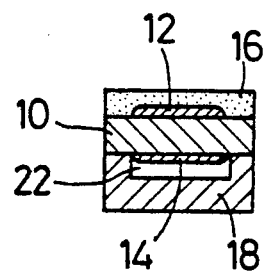
FIGS. 2, 4, 6, 8 and 10 are schematic elevational views in cross section taken along lines A—A' of FIG. 1, B—B' of FIG. 3, C—C' of FIG. 5, D—D' of FIG. 7 and E—E' of FIG. 9, respectively.

There is first shown in the exploded perspective view of FIG. 1 a basic arrangement of an oxygen concentration sensing element which is one form of an electrochemical element of the invention. A detecting portion of the sensing element at which electrodes are disposed is illustrated in FIG. 2 in transverse cross section.

In the figures, the oxygen concentration sensing element (oxygen sensor) comprises a planar solid electrolyte substrate in the form of a partially-stabilized zirconia ceramic layer 10, and a pair of electrodes 12, 14, i.e., a measuring electrode 12 and a reference electrode 14, which are disposed on opposite surfaces of the partially-stabilized zirconia ceramics layer 10 such that the two electrodes 12, 14 are aligned with each other. These electrodes 12, 14 are formed of porous layers of platinum or a similar material. A porous layer 16 of fully-stabilized zirconia ceramic is formed on the partially-stabilized zirconia ceramic layer 10, so as to cover the measuring electrode 12. On the side of the partially-stabilized zirconia ceramic layer 10 on which the reference electrode 14 is disposed, there is formed a gas-tight spacer layer 18 made of zirconia or the like. The spacer layer 18 has a reference-gas passage 20 which is open at its one end to the ambient air, or connected at that end to a source of other reference gas, so that the reference electrode 14 is exposed to ambient air or another reference gas of a known oxygen concentration which is introduced in the reference-gas passage 20.

In the aforementioned oxygen concentration sensing element, the measuring electrode 12 is exposed to a measurement gas via the porous protective layer 16, while the reference electrode 14 is exposed to ambient air or other reference gas. Based on a difference in oxygen concentration between the measurement gas and the reference gas, an electromotive force is induced between the measuring and reference electrodes 12, 14. The induced electromotive force is measured, in the same manner as practiced in known oxygen sensors, by an external measuring apparatus such as a potentiometer 24 to which the electrodes 12, 14 are connected through their leads.

With the foregoing arrangement of the oxygen concentration sensing element, the solid electrolyte substrate 10 made of partially-stabilized zirconia ceramics is excellent in mechanical strength, and is highly resistant to thermal stress upon an abrupt change in temperature of the measurement gas or rapid heating of the element by a heater. Thus, the solid electrolyte substrate 10 is protected from cracking due to thermal stress. In addition, the porous protective layer 16 made of fully-stabilized zirconia ceramics is highly stable at elevated temperatures, and is therefore protected from internal destruction or collapse of its porous structure which may be originated from micro cracking on its surface. Furthermore, the porous protective layer 16 is protected from flake-off or separation from the partially-stabilized zirconia ceramic substrate layer 10, which could take place due to a difference in thermal expansion. The partially-stabilized zirconia ceramic layer 10 may be made of a known zirconia ceramic of a composite phase of cubic crystal and monoclinic crystal, or of a composite phase of cubic crystal, monoclinic crystal and tetragonal crystal. Preferably, the partially-stabilized zirconia ceramic layer 10 consists substantially of a zirconia ceramic having a tetragonal crystal phase, or a composite phase of tetragonal crystal and cubic crystal. In this case, the rate of thermal expansion of the partially-stabilized zirconia ceramic layer 10 may be made substantially equal to that of the fully-stabilized zirconia ceramic layer 16, which is typically made of zirconia ceramics having a cubic crystal phase. Accordingly, the electrochemical element may be formed as a laminar or multi-layer structure which suffers minimum thermal troubles such as separation or flake-off of the layers due to thermal stress upon rapid heating or cooling of the laminar structure.

While it is possible to use known partially-and fully-stabilized zirconia ceramic materials for the solid electrolyte layer 10 and porous protective layer 16 of the laminar electrochemical element, respectively, it is preferred that the solid electrolyte layer 10 be made substantially of zirconia ceramics having a of tetragonal crystal phase (structure) or of composite phase (structure) of tetragonal crystal and cubic crystal, while the porous layer 16 be made substantially of zirconia ceramic having a cubic crystal phase (structure), as discussed above. For example, partially-stabilized zirconia ceramic may consist of: 97 mole % of $ZrO_2$ and 3 mole % of $Y_2O_3$; 95 mole % of $ZrO_2$ and 5 mole % of $Y_2O_3$, and 0.1 part by weight of $Al_2O_3$ per 100 parts by weight of $ZrO_2$ and $Y_2O_3$; or 97 mole % of $ZrO_2$ and 3 mole % of MgO. On the other hand, fully-stabilized zirconia ceramic may consists of: 90 mole of $ZrO_2$ and 10 mole % of $Y_2O_3$; 85 mole % of $ZrO_2$ and 15 mole % of CaO; or 90 mole % of $ZrO_2$ and 10 mole % of $Yb_{2l}O_3$.

The laminar structure of the oxygen concentration sensing element described hitherto may be fabricated in various known processes. For example, the electrodes and their leads, and other layers are formed on green sheets of the zirconia ceramic layers, with suitable methods such as screen printing, slurry coating, spraying, transfer printing or other processes. Additional green sheets may be used as needed. An unfired laminar structure of superposed layers is co-fired. Alternatively, a green sheet of the partially-stabilized zirconia ceramic layer is first fired, and the other layers are formed on the surfaces of the fired zirconia ceramics layer, one after another with intermittent baking processes for firing the individual layers. In another method, the green sheet of the partially-stabilized zirconia ceramic substrate is first pre-fired or calcined, and the other layers are formed on the pre-fired or calcined substrate, followed by final co-firing of the laminar structure. It is also possible that the partially-stabilized zirconia ceramic substrate is first fired, and then the electrode layers, fully-stabilized zirconia ceramics layer, and other layers are formed by using a plasma spraying, sputtering, CVD or another process.

In the case where the electrodes 12, 14 and their leads are co-fired or fired concurrently with the other layers, the electrodes and leads are formed by printing, using as major components thereof at least one element selected from the platinum group which includes platinum, palladium, rhodium, iridium, ruthenium and osmium. In this connection, it is desired to admix fine particles of ceramics such as zirconia and alumina, with the materials of the electrodes and leads, for improving the adhesion of the electrodes and leads to their contacting layers. For instance, it is possible to use a mixture of particles which consists of 60% by volume of Pt and 40% by volume of $ZrO_2$.

Figure 3:
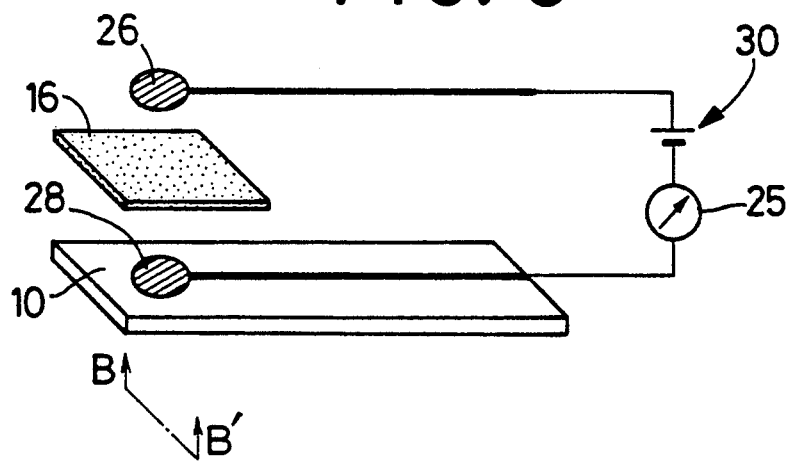

While one form of electrochemical element according to the invention has been illustrated referring to FIGS. 1 and 2, the invention may be embodied in various other forms as illustrated in FIG. 3 et seq., within the scope defined in the appended claims.

Figure 4:
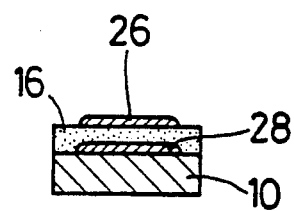

An electrochemical element shown in FIGS. 3 and 4 is an oxygen concentration sensing element similar to that of FIGS. 1 and 2, and is referred to as oxygen sensor of so-called limiting current type.

Described more specifically, a pair of pumping electrodes 26, 28 are disposed on opposite sides of the porous layer 16 of a fully-stabilized zirconia ceramic, in aligned relation with each other. The pumping electrodes 26, 28 are connected through their leads to an external power source 30, so that a flow of current between the electrodes 26, 28 will cause an electrochemical pumping action to move oxygen ions from the inner side of the porous layer 16 toward the outside, and thereby discharge the oxygen ions. Namely, the porous fully-stabilized zirconia ceramic layer 16 and the pair of electrodes 26, 28 constitute an electrochemical pumping cell. In this embodiment, the gas-tight layer 10 of partially-stabilized zirconia ceramic functions as a support for supporting the electrochemical pumping cell. The inner pumping electrode 28 is disposed between and in contact with this gas-tight layer 10 of partially-stabilized zirconia ceramic and the porous layer 16 of fully-stabilized zirconia ceramic.

In the oxygen concentration sensing element thus constructed, oxygen which has been diffused from the surrounding measurement gas to the inner pumping electrode 28 through the porous fully-stabilized zirconia ceramic layer 16, is pumped out of the sensing element by means of an electrochemical pumping action by the pumping cell which is constituted by the porous layer 16 of fully-stabilized zirconia ceramic and the two pumping electrodes 26, 28. As a result, an electric current flows between the electrodes 26, 28 in an amount corresponding to an amount of oxygen pumped out through the porous layer 16. Hence, the oxygen concentration of the measurement gas may be detected by measuring an amperage of an ammeter 25 connected to the electrodes.

As described above, the porous fully-stabilized zirconia ceramic layer 16 of the oxygen concentration sensing element serves as a diffusion layer with a predetermined diffusion resistance, through which the oxygen is diffused from the surrounding measurement gas toward the inner pumping electrode 28. At the same time, the porous layer 16 functions as a solid electrolyte layer which performs a pumping action with a current flowing between the two electrodes. As previously indicated, the utilization of fully-stabilized zirconia ceramic for the porous layer 16 permits minimization of microcracking on the surfaces of the porous structure of the layer 16, and prevention of physical deterioration of the porous structure, thereby effectively restraining changes in diffusion resistance to molecules of oxygen and in electrical resistance of the porous layer 16. Therefore, the use of fully-stabilized zirconia ceramic provides effective means for avoiding reduction in measuring accuracy of the electrochemical element due to otherwise changes in the diffusion resistance and electrical resistance of the porous layer 16 during service of the electrochemical element.

In the case where the porous fully-stablized zirconia ceramic layer 16 is used as a diffusion layer having a predetermined diffusion resistance, the porosity of the porous layer 16 is suitably selected depending upon the required level of diffusion resistance. If the porous layer 16 is formed in a sintering process, the porosity is preferably held within a range of approx. 2–30% as measured according to a mercury porosimetric method (using Mercury Porosimeter Type 70H available from Carlo Erba, Italy). If a plasma spraying process is used to form the porous layer 16, a preferred range of the porosity is between 0.5% and 10% approx., as measured according to the same method.

Although the partially-stabilized zirconia ceramic layer 10 must have greater gas tightness than the porous diffusion layer 16 of fully-stabilized zirconia ceramic, the layer 10 must not be completely gas-tight. In other words, the partially-stabilized zirconia ceramic layer 10 may be slightly permeable to a measurement component (oxygen) of the surrounding measurement atmosphere, provided that the permeability of the layer 10 will not have an adverse effect on the atmosphere surrounding the inner pumping electrode 28, i.e., on the atmosphere which has been diffused through the porous structure of the fully-stabilized zirconia ceramic layer 16. In other words, the layer 10 should be gas-tight only to such an extent that the amount of oxygen to be moved toward the outer pumping electrode 26 under an electrochemical pumping action will not be significantly affected by the permeable nature of the layer 10.

Figure 5:
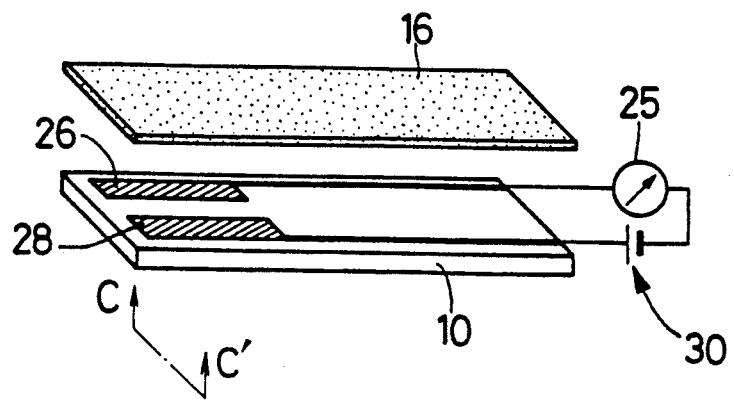
Figure 6:
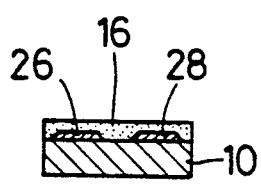

A third embodiment of the oxygen concentration sensing element of the invention is shown in FIGS. 5 and 6, which is an oxygen sensor of a limiting current type similar to the second embodiment of FIGS. 3 and 4. This third embodiment is characterized by the pair of electrodes 26, 28 which are both sandwiched between and in contact with the partially-stabilized zirconia ceramic layer 10 and the porous fully-stabilized zirconia ceramic layer 16.

Stated in more detail, the two electrodes 26 and 28 are disposed in a juxtaposed relation with each other, along the length of the layer 10. With electric power applied to the juxtaposed electrodes 26, 28, a pumping current flows between the electrodes 26, 28 through the lower and upper partially-stabilized and fully-stabilized zirconia ceramic layers 10, 16, whereby oxygen ions are moved, under an electrochemical pumping action, from one of the pumping electrodes (pumping electrode 26, in this example) toward the other pumping electrode (electrode 28, in the example). Also, the oxygen in the measurement gas is diffused through the porous diffusion layer 16 of fully-stabilized zirconia ceramic, toward the pumping electrode 26. Thus, the oxygen concentration of the measurement gas may be measured as previously described.

Figure 8:
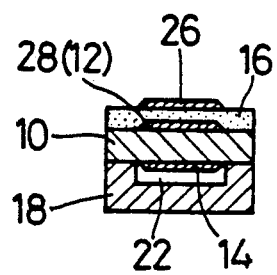
Figure 7:
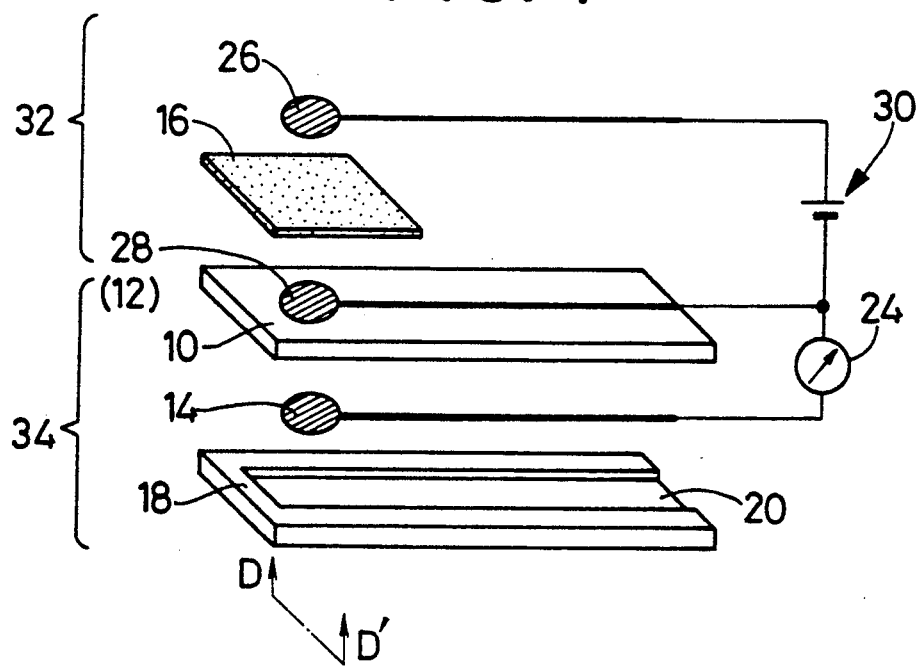

FIGS. 7 and 8 represent a fourth embodiment of the electrochemical element of the invention, wherein two electrochemical cells are formed by using the partially-stabilized zirconia ceramic layer 10 and the porous fully-stabilized zirconia ceramic layer 16.

More particularly, an electrochemical oxygen pumping cell 32 is constituted by the porous layer 16 of fully-stabilized zirconia ceramic and the pair of pumping electrodes 26, 28 disposed in contact with the opposite surfaces of the porous layer 16, and in aligned relation with each other. On this pumping cell 32, there is formed an electrochemical oxygen concentration sensing cell 34 which is constituted by the gas-tight layer 10 of partially-stabilized zirconia ceramic, and the pair of electrodes 12, 14 which are disposed in contact with the opposite surfaces of the gas-tight layer 10, and in an aligned relationship with each other. It is noted that a single electrode layer serves commonly as the inner pumping electrode 28 and the measuring electrode 12 which are interposed between the gas-tight layer 10 of the sensing cell 34 and the porous layer 16 of the pumping cell 32.

In the oxygen pumping cell 32 of the electrochemical element of FIGS. 7 and 8, the porous layer 16 of a fully-stabilized zirconia ceramic functions as a diffusion layer for a pumping action by means of the two pumping electrodes 26, 28 on the opposite sides of the layer 16. The oxygen concentration of the atmosphere surrounding the inner pumping electrode 28, i.e., surrounding the measuring electrode 12 of the oxygen concentration sensing cell 34, is controlled by the pumping cell 32. In the oxygen concentration sensing cell 34, the potentiometer 24 measures an electromotive force which is induced due to a difference in oxygen concentration between the controlled atmosphere contacting the measurement electrode 12, and the ambient air or other reference gas contacting the reference electrode 14.

In this embodiment, too, the fully-stabilized zirconia ceramic layer 16 serves, on the one hand as a diffusion layer, and on the other hand as a solid electrolyte layer through which a pumping current flows. This layer 16 is highly stable at high temperatures, that is, subject to minimum physical deterioration of its porous structure during its service, and consequently subject to small changes in diffusion resistance and electrical resistance. Therefore, the initial measuring accuracy of the electrochemical element may be maintained for a longer period of time.

Figure 9:
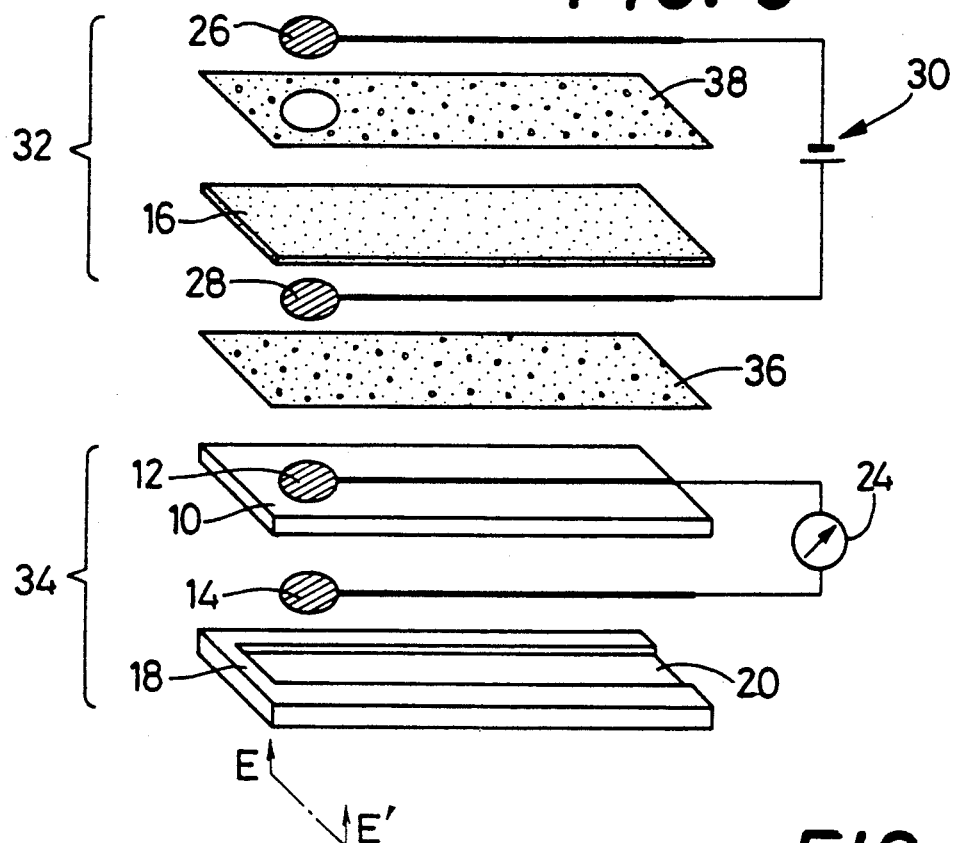
Figure 10:
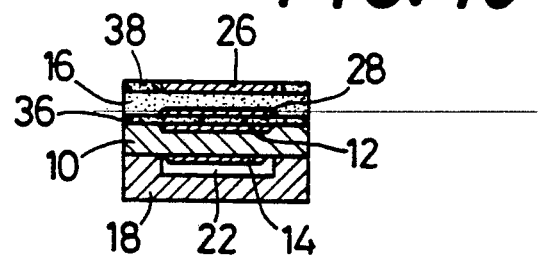

A fifth embodiment of the electrochemical element of the invention is illustrated in FIGS. 9 and 10, which is suitably used as a so-called "rich-burn" sensor for measuring the oxygen concentration of fuel-rich exhaust gases whose oxygen partial pressure is lower than that of the stoichiometric air-fuel ratio.

Like the preceding fourth embodiment, this fifth embodiment comprises an oxygen pumping cell 32 using the porous layer 16 of fully-stabilized zirconia ceramic, and an oxygen concentration sensing cell 34 using the partially-stabilized zirconia ceramic layer 10. These two electrochemical cells 32, 34 are superposed on each other with a porous electrical insulating layer 36 sandwiched therebetween, so as to provide a laminar structure. Reference numeral 38 designates a porous electrical insulating layer for protecting leads of the outer pumping electrode 26 of the oxygen pumping cell 32.

In the electrochemical element described above, the fully-stabilized zirconia ceramic layer 16 of the pumping cell 32 functions as a diffusion layer through which a fuel component of the measurement gas is diffused to the inner pumping electrode 28, while the oxygen ions are moved to the inner pumping electrode 28 with a pumping voltage applied between the two pumping electrodes 26, 28, so that the fuel component of the atmosphere surrounding the inner pumping electrode 28 is burned to neutralize the atmosphere. The neutralized atmosphere is moved through the porous insulating layer 36 and brought into contact with the measuring electrode 12. An electromotive force between the measuring electrode 12 and the reference electrode 14 exposed to the reference gas is measured by the potentiometer 24.

While the instant embodiment uses the gas-permeable porous electrical insulating layer 36 between the two cells 32, 34, i.e., between the fully and partially-stabilized zirconia ceramic layers 16 and 10, this insulating layer 36 is formed with a small thickness so that the presence of the insulating layer 36 is almost negligible in terms of its influence on the possibility of separation or flake-off of the two cells 32, 34. The thickness of the electrical insulating layer 36 is generally held less than 300 microns, preferably within a range of 10–200 microns approximately.

Figure 11:
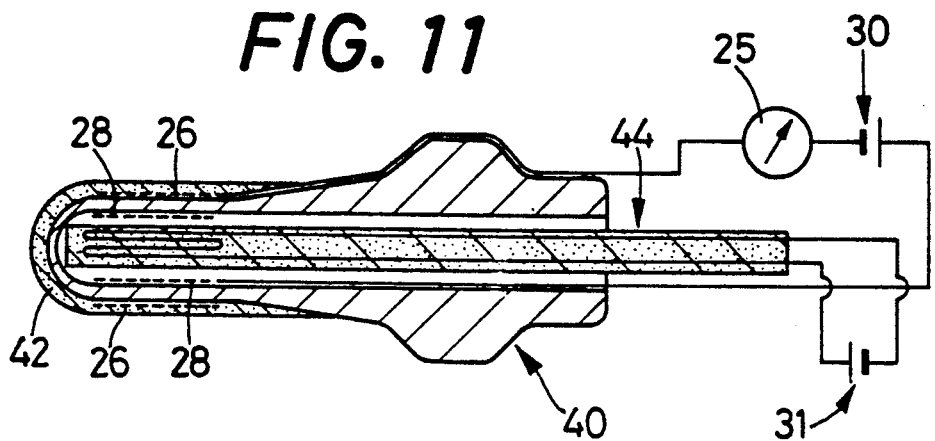
FIG. 11 is a cross sectional view of another embodiment of an electrochemical element of the invention.

A sixth embodiment of the electrochemical element of the invention is depicted in FIG. 11, which is an oxygen sensor of a tubular configuration, wherein a pair of annular electrodes 26, 28 are provided in contact with outer and inner surfaces of a tubular layer 40 of partially-stabilized zirconia ceramic which is closed at its one end. The outer electrode 26 is covered by a porous tubular layer 42 of fully-stabilized zirconia ceramic. In a longitudinal bore formed in the tubular layer 40, there is inserted a ceramic bar of an electrical heater 44 which comprises a conductor pattern of tungsten embedded in alumina ceramic, so that the electrodes 26, 28 may be maintained at suitable elevated operating temperatures.

In the above oxygen concentration sensing element, oxygen in the surrounding measurement gas is diffused through the porous layer 42 of fully-stabilized zirconia ceramic and brought into contact with the electrode 26. The diffused oxygen is then pumped into the longitudinal bore in the tubular layer 40 of partially-stabilized zirconia ceramic, by means of an pumping action by the pumping cell constituted by the tubular layer 40 and the two electrodes 26, 28, with an electric current supplied from by the external power source 30. The oxygen concentration of the measurement gas is measured by the ammeter 25. When the element is heated by the heater 44 connected to an eternal power source 31, the impedance of the pumping cell is lowered, whereby it is possible to measure the oxygen concentration of a measurement gas whose oxygen content is relatively high.

While the present invention has been described in its several preferred embodiments, it is to be understood that the electrochemical element of the invention is not confined to the precise disclosure of the illustrated embodiments, but the invention may be otherwise embodied with various changes, modifications and improvements which may occur to those skilled in the art, in the light of the foregoing teachings, and without departing from the scope of the invention defined in the accompanying claims.

In the interest of brevity and easy understanding, a heater layer is not shown in the illustrated electrochemical elements of planar configuration. However, it is possible and advantageous to provide such electrochemical elements of planar laminar structure with a suitable heater layer as known in the art, for heating the solid electrolyte layer of zirconia ceramic and the electrodes. The heater layer assures reliable and accurate operation of the electrochemical element even while the temperature of an exhaust gas or other measurement gas is low and the solid electrolyte is not maintained at a sufficiently high operating temperature. The provision of a heater layer is desired particularly for such electrochemical elements that comprise a pumping cell using a porous layer of fully-stabilized zirconia ceramic, in order to provide the pumping cell with a sufficient pumping capability.

Although the electrochemical element according to the invention is suitably used as an oxygen sensor as illustrated herein, the present invention may be embodied as sensors or controllers for determining or controlling the concentration of specific components, other than oxygen, of a fluid associated with electrode reaction, such as nitrogen, carbon dioxide and hydrogen.

What is claimed is:

1. An electrochemical element having a laminar structure, comprising:
   a porous first layer of a fully-stabilized zirconia ceramic consisting essentially of a cubic crystal phase;
   a second layer of a partially-stabilized zirconia ceramic consisting essentially of a tetragonal crystal phase and functioning as a substrate of the electrochemical element; and
   at least one pair of electrodes, at least one of said at least one pair of electrodes being disposed between said porous first layer and said second layer, and being in contact with said porous first layer, said porous first layer functioning as a protective layer for said at least one electrode and being a diffusion layer having a predetermined diffusion resistance;
   wherein said at least one of said at least one pair of electrodes, said porous first layer and said second layer constitute a co-fired laminar structure in which a portion of said porous first layer around said at least one of said at least one pair of electrodes and a corresponding portion of said second layer around said at least one electrode are in direct contact with each other.

2. An electrochemical element as recited in claim 1, wherein said porous first layer functions as a protective layer for said at least one electrode.

3. An electrochemical element as recited in claim 1, wherein said porous first layer functions as a diffusion layer having a predetermined diffusion resistance.

4. An electrochemical element as recited in claim 1, wherein said porous first layer functions as a diffusion layer having a predetermined diffusion resistance, and as a solid electrolyte layer through which a pumping current flows between said pair of electrodes.

5. An electrochemical element as recited in claim 1, wherein said at least one pair of electrodes are disposed on opposite sides of said second layer of partially-stabilized zirconia ceramic.

6. An electrochemical element as recited in claim 1, wherein said at least one pair of electrodes are disposed on opposite sides of said porous first layer of fully-stabilized zirconia ceramic, in an aligned relationship with each other.

7. An electrochemical element as recited in claim 1, wherein said at least one pair of electrodes comprises a first pair of electrodes which are disposed on opposite sides of said second layer, and a second pair of electrodes which are disposed on opposite sides of said porous first layer in an aligned relationship with each other.

8. An electrochemical element as recited in claim 7, wherein a single electrode is disposed between said first and second layers, said single electrode serving commonly as one of said first pair of electrode, and as one of said second pair of electrodes.

9. An electrochemical element having a laminar structure, comprising:
   a porous first layer of a fully-stabilized zirconia ceramic consisting essentially of a cubic crystal phase;
   a second layer of a partially-stabilized zirconia ceramic consisting essentially of a tetragonal crystal phase and functioning as a substrate of the electrochemical element; and
   a first pair of electrodes which are disposed on opposite sides of said second layer and a second pair of electrodes which are disposed on opposite sides of said porous first layer in an aligned relationship with each other, said porous first layer functioning as a protective layer for one of said second pair of electrodes and being a diffusion layer having a predetermined diffusion resistance;
   wherein said one of said second pair of electrodes, said porous first layer and said second layer constitute a co-fired laminar structure in which a portion of said porous first layer around said at least one of said at least one pair of electrodes and a corresponding portion of said second layer around said one electrode are in direct contact with each other.

10. A method of producing an electrochemical element comprising:
    providing a substrate consisting of a partially-stabilized zirconia ceramic consisting essentially of a tetragonal crystal phase;
    depositing at least one pair of electrodes on opposite sides of said substrate;
    depositing a porous layer consisting of a fully-stabilized zirconia ceramic consisting essentially of a cubic crystal phase on said substrate, such that at least one of said at least one pair of electrodes is disposed between said porous layer and said substrate and is in contact with said porous layer; and
    co-firing said porous layer, said at least one of said at least one pair of electrodes and said substrate to form a laminar structure in which a portion of said porous layer around said at least one of said at least one pair of electrodes and a corresponding portion of said substrate around said at least one electrode are in direct contact with each other.

* * * * *